(12) United States Patent
Ross et al.

(10) Patent No.: US 9,925,016 B2
(45) Date of Patent: Mar. 27, 2018

(54) MEDICAL SUPPORT STRUCTURE

(71) Applicants: Jonathan James Ross, Sheffield (GB); Timothy John Hulley, Sheffield (GB)

(72) Inventors: Jonathan James Ross, Sheffield (GB); Timothy John Hulley, Sheffield (GB)

( * ) Notice: Subject to any disclaimer, the term of this patent is extended or adjusted under 35 U.S.C. 154(b) by 0 days.

(21) Appl. No.: 15/298,628

(22) Filed: Oct. 20, 2016

(65) Prior Publication Data
US 2017/0105808 A1 Apr. 20, 2017

(30) Foreign Application Priority Data
Oct. 20, 2015 (GB) .................................. 1518596.0

(51) Int. Cl.
| | | |
|---|---|---|
| A47B 85/00 | (2006.01) |
| A61B 50/30 | (2016.01) |
| B62B 3/00 | (2006.01) |
| B65F 1/14 | (2006.01) |
| A61M 5/52 | (2006.01) |

(52) U.S. Cl.
CPC ........... A61B 50/3001 (2016.02); A61M 5/52 (2013.01); B62B 3/002 (2013.01); B65F 1/141 (2013.01)

(58) Field of Classification Search
CPC ...... A61B 50/3001; A61M 5/52; B62B 3/002; B65F 1/141
See application file for complete search history.

(56) References Cited

U.S. PATENT DOCUMENTS

| | | | | |
|---|---|---|---|---|
| 3,126,101 | A | * | 3/1964 | Katterjohn ............. A47B 57/06 211/133.1 |
| 3,385,329 | A | | 5/1968 | Kellermeier, Jr. |
| 3,853,289 | A | | 12/1974 | Nevermann et al. |
| 4,117,937 | A | * | 10/1978 | Ratti ...................... A47B 57/04 211/189 |
| 4,391,454 | A | | 7/1983 | Marsh et al. |
| 4,917,250 | A | * | 4/1990 | Barbieri ................. A47B 57/04 211/149 |
| 5,048,699 | A | * | 9/1991 | Trevaskis ............... A47B 57/14 211/128.1 |

(Continued)

FOREIGN PATENT DOCUMENTS

| | | |
|---|---|---|
| CN | 204501391 U | 7/2015 |
| FR | 2837379 B1 | 7/2004 |

(Continued)

*Primary Examiner* — Hanh V Tran
(74) *Attorney, Agent, or Firm* — GrayRobinson, P.A.

(57) ABSTRACT

A medical support structure is disclosed, which comprising a framework having a main axis and comprising at least one supporting member and a plurality of leg members, and a top surface locatable atop the framework and adapted to support one or more refuse containers each having an aperture and a bottom portion. The supporting member is locatable intermediate the top surface and a lower portion of the plurality of leg members, and is adapted to support at least one medical waste container having an aperture and a bottom portion. At least a first longitudinal portion of the supporting member forms an obtuse angle relative to a second longitudinal portion of the supporting member so as to angle the or each medical waste containers in a position in which its aperture is higher than its bottom portion but not orthogonal to the top surface.

15 Claims, 15 Drawing Sheets

(56) References Cited

U.S. PATENT DOCUMENTS

| | | | |
|---|---|---|---|
| 5,090,587 A * | 2/1992 | Brown | A47F 5/0018 211/81 |
| 5,688,034 A * | 11/1997 | Kojima | A47B 57/04 211/175 |
| 5,765,842 A | 6/1998 | Phaneuf et al. | |
| 6,321,663 B1 * | 11/2001 | Rogers | A47B 43/00 108/100 |
| 6,948,900 B1 * | 9/2005 | Neuman | B62B 3/002 193/35 R |
| 9,004,300 B1 * | 4/2015 | Morrell | A47F 5/137 108/107 |
| 2003/0218308 A1 * | 11/2003 | Lamson | B62B 3/002 280/79.3 |
| 2004/0090028 A1 * | 5/2004 | Trogstam | A01K 1/031 280/79.3 |
| 2005/0211648 A1 * | 9/2005 | Haller | A47B 57/04 211/75 |
| 2006/0144805 A1 * | 7/2006 | Wang | A47B 57/04 211/37 |
| 2007/0018059 A1 | 1/2007 | Woodcock | |
| 2007/0068942 A1 | 3/2007 | Smudde | |
| 2007/0252496 A1 * | 11/2007 | Remondino | A47B 57/04 312/351 |
| 2007/0278140 A1 * | 12/2007 | Mallett | B07C 7/005 705/308 |
| 2008/0197059 A1 | 8/2008 | Mallett et al. | |
| 2009/0272859 A1 * | 11/2009 | Pippin | B07C 7/00 248/99 |
| 2012/0024575 A1 | 2/2012 | Zhang et al. | |
| 2013/0220957 A1 * | 8/2013 | Malik | A47B 57/04 211/119.004 |
| 2016/0015388 A1 * | 1/2016 | Ren | A61B 17/06161 383/33 |

FOREIGN PATENT DOCUMENTS

| | | |
|---|---|---|
| GB | 1322403 A | 7/1973 |
| GB | 2314004 A | 12/1997 |

* cited by examiner

MEDICAL SUPPORT STRUCTURE

CROSS-REFERENCE TO RELATED APPLICATIONS

This application claims priority from Great Britain patent application number 1518596.0, filed Oct. 20, 2015, the disclosure of which is hereby incorporated by reference herein.

BACKGROUND OF THE INVENTION

Field of the Invention

The present invention relates to improvements in medical support structures for use in medical environments. More particularly, the present invention relates to a multifunctional medical support structure for facilitating the streaming of refuse during medical procedures.

Background Art

Many medical support structures are known and used within healthcare environments. A wide variety of such structures have been developed for function-specific purposes, and include medical carts or trolleys developed to assist surgical or treatment procedures as disclosed in e.g. U.S. Pat. No. 5,765,842; carts or trolleys adapted to store and transport refuse as disclosed in e.g. U.S. Pat. No. 3,853,329; carts or trolleys adapted to facilitate laundry-related tasks as disclosed in e.g. GB 1322403; modular carts or trolleys developed to assist with one or more of the above examples, as disclosed in e.g. WO 2012024575; besides generic carts or trolleys adapted to store and transport all manner of medical and non-medical goods and/or refuse, as disclosed in e.g. FR 2837379.

The development of medical support structures, mobile or otherwise, continues apace, particularly under the influence or ever stricter statutory or regulatory imperatives in the respective fields of hygiene and environmental preservation.

In recent times, several outbreaks of hospital-acquired infection (HAI), also known as nosocomial infection and associated with viral, bacterial, and fungal pathogens, have underlined the requirement to maintain all equipment within healthcare environments in the cleanest possible condition at all times, both to inhibit and mitigate bacteriological contamination, and many of the prior art medical trolleys exhibit aspects of shape and configuration which render their thorough cleaning difficult, because they include numerous angles, corners, blind apertures and the like that are difficult to reach with conventional cleaning implements.

In parallel to and partial association with the above, environmental regulations have been promulgated in respect of medical and non-medical waste, particularly that contaminated by potentially infectious bodily fluids, which require sorting of waste onsite according to waste type in a variety of medical and non-medical waste containers, for optimal processing both within the healthcare environment and, subsequently, beyond. Waste generated in healthcare procedure is a mixture of domestic-like waste which requires relatively simple and inexpensive processing for disposal; and clinical or hazardous waste which requires more complex, energy-dependent and onerous processing, typically incineration for disposal. Keeping both types of waste apart through streaming during their generation stops the domestic-like waste from becoming contaminated by the clinical or hazardous type of waste, and thus prevents more, originally non-clinical or hazardous, waste from having to be processed with the more complex procedure. Practically, such sorting typically involves transporting any contaminated equipment and waste away from a treatment site or operating table after use, to a refuse container located a short distance away for picking and streaming thereat during or after completing a procedure.

It is for instance well-known to dispose of "sharps" such as disposable scalpels, syringes and other implements with needles thereon and the like in "sharps containers" having a top aperture facilitating the dropping of sharps therein without touching the outside of the container, and otherwise forming a sealed unit designed to inhibit accidental spillage of medical needles and other instruments therein after their insertion. Such medical waste containers are subsequently disposed of with the medical waste inside, or reused after emptying and sterilisation, under strictly controlled conditions.

The medical support structures of the prior art are ergonomically suboptimal, since any sharps containers may only be rested thereon in a conventional manner, i.e. with their bottom surface abutting a top surface or underlying surface of the trolley with the sharps container upstanding orthogonally to that surface. As a practitioner or nurse disposes of medical waste during a procedure, there is accordingly a risk that a sharps container may be knocked over and, though not discharging its instrumental contents, may nevertheless spill any liquid waste present therein back out through the top aperture.

Accordingly, there is a requirement to improve the supporting of medical waste containers on a medical support structure located adjacent a healthcare or surgical treatment site, such as a surgical table or emergency treatment location, mitigating at least the above disadvantages of prior art carts and trolleys.

SUMMARY OF THE INVENTION

The present invention aims to mitigate the ergonomic limitations of prior art carts, trolleys and tables and to assist in streaming medical refuse during procedures by providing a multifunctional support structure for medical, nursing and other healthcare tasks with improved supporting means for refuse containers, including medical waste containers such as sharps container, that facilitate real time streaming and disposal of dangerous items by a clinician and/or assisting personnel immediately adjacent the treatment site, accordingly reducing handling and spillage risks associated with such dangerous items.

According to an aspect of the present invention, there is therefore provided a medical support structure comprising a framework having a main axis and comprising at least one supporting member and a plurality of leg members; and a top surface locatable atop the framework, adapted to support one or more refuse containers each having an aperture and a bottom portion, wherein the at least one supporting member is locatable intermediate the top surface and a lower portion of the plurality of leg members, and adapted to support at least one medical waste container having an aperture in an upper portion thereof, wherein at least a first longitudinal portion of the supporting member forms an obtuse angle relative to a second longitudinal portion of the supporting member so as to angle the or each supported medical waste container non-orthogonally relative to the top surface in use, and wherein a portion of the top surface area is recessed above the or each supported medical waste container.

The angle of the supporting member portions advantageously allows medical waste containers to be supported thereon through their lateral wall rather their bottom surface, thus decreasing their upstanding profile, which helps mitigate risks of accidental knocking. Moreover, the angling of the containers on the support member also orients their top aperture partially towards an adjacent clinician, in an ergonomically optimal manner for disposing of medical waste with streaming same ad hoc across a variety of containers, and so reducing the risk of contaminating sterile gloves or gowns of adjacent staff. The recessed portion of the top surface advantageously further facilitates disposal of medical waste and streaming same ad hoc across a variety of containers, as the recessed portion of the top surface facilitates unimpeded access thereto, that may otherwise be partially occluded by the top surface.

Accordingly, in a preferred embodiment of the structure according to the invention, the or each supporting member supports a plurality of medical waste containers to facilitate streaming of medical refuse and mitigate the risk of initially non-hazardous refuse or waste being made hazardous by inadvertent contamination.

In an embodiment of the structure according to the invention, corners at opposed ends of the top surface have a substantially curvilinear shape. This embodiment advantageously reduces the risk of acutely-shaped corners damaging or tearing the refuse containers supported by the top surface, and facilitates thorough cleaning of the periphery of the top surface, besides reducing the risk of injury to staff if they should accidentally impact the top surface corners.

In an embodiment of the structure according to the invention, a transversal orientation of the or each supporting member is adjusted relative to the main axis of the framework, to vary the orientation of the top aperture of the supported containers relative to the structure, as a function of the structure's dimensions and height of the supporting member, and the expected or increasing amount of liquid contents of one or more containers.

In an embodiment of the structure according to the invention, the or each support member further comprises a drip tray located substantially underneath the aperture of the or each medical waste container. This further feature advantageously helps mitigate accidental low velocity spillage of medical waste from the supported containers onto an underlying floor.

In an embodiment of the structure according to the invention, the or each support member further comprises transverse end flanges to protect containers supported thereon. The flanges advantageously help prevent accidental dislodgement of containers from the supporting member, if the structure should be accidentally knocked or pushed longitudinally.

In an embodiment of the structure according to the invention, a surface of the or each support member comprises at least one lodgement for accommodating a lower portion of a medical waste container therein. Such lodgements may be dimensioned according to standard or prevalent cross-sectional sizes of medical waste containers. Such lodgement(s) facilitate the locating of medical waste containers on the supporting member and their releasable securing in place during use.

In an embodiment of the structure according to the invention, at least one end of the top surface comprises a downwardly-angled flange, and a portion of a refuse container wall adjacent the aperture thereof is secured to the downwardly-angled flange with releasable securing means. In a variant of this embodiment, the releasable securing means may be one or more magnets. In a particularly simple and useful embodiment, the magnet material is neodymium.

These configurations advantageously take advantage of the natural shape adopted by refuse containers of medium to large capacity, such as refuse bags typically made of thin plastics material, when retained upright by a peripheral portion of their top aperture, wherein the remainder of the peripheral wall either side of the retaining location effectively sags partially open. Retaining a portion of the refuse container top wall by maintaining it captive of the flange through magnetic force provides a simple retaining solution with no articulated or moving parts, allowing for very easy cleaning. The downward shape of the flange leading into the open top aperture of the refuse container also biases any spillage on the top surface adjacent thereto into the refuse container.

An embodiment of the structure according to the invention may further comprise a base locatable intermediate the, or a lowest, supporting member and the lower portion of the plurality of leg members. In a variant of this embodiment, at least one end of the base may comprise an upwardly-angled flange, and the bottom portion of a refuse container rests upon the base inwardly of the upwardly-angled flange. The bottom portion of a refuse bag maintained by the downwardly-oriented flange is advantageously supported by the base member to prevent both stretching of the bag under the weight of the refuse therein and a gradual closure of the top aperture as a result of such stretching. The provision of an upwardly-oriented flange prevents both accidental puncture of the refuse container adjacent its bottom portion and any accidental pendulum movement thereof during any motion of the structure, deliberate or accidental.

In an embodiment of the structure according to the invention, a height of each leg members may be adjustable, for instance as a function of any one or more factors including the clinician's height or physique in relation to the structure's dimensions and height of the supporting member.

In an embodiment of the structure according to the invention, at least one leg member extends through and above the top surface. The projecting portion of the leg member may advantageously support any medical or non-medical device, apparatus or container above and clear of the top surface, such as a patient heart rate monitor or an intravenous solution bag or the like.

In an embodiment of the structure according to the invention, the plurality of leg members comprises at least one pair of transversally-opposed leg members, a lowest extremity of each of which comprises a wheel. In a variant of this embodiment, each wheel may be an antistatic wheel. This configuration advantageously facilitates positional adjustment of the structure and its transporting onsite.

In an alternative embodiment, a lowest extremity of each leg may instead comprise a skid member. This configuration is considered particularly useful for embodiments intended for field use by first responders to emergencies, whether of the disposable type or reusable type.

In an embodiment of the structure according to the invention, components of the structure are adapted both for self-assembly and self-disassembly by a user and for storage in low volume packaging. This embodiment is intended for stowage in emergency vehicles and comparable environments of reduced stowage capacity, in which components of the structure are adapted for rapid assembly and deployment at emergency treatment sites. Such embodiments may be disposable, with components shaped and/or configured primarily for ease of assembly, and for instance made of inexpensive recycled materials for ease and thoroughness of combustion when disposed. Alternatively, such embodiments may be re-usable, with components shaped and/or configured for ease of both assembly and disassembly, and for instance made of durable and easily cleanable materials such as stainless steel or thermoplastics Accordingly, one or more of the framework, top surface and one or more supporting member is made of a ferrous material, stainless steel, a plastics material such as polycarbonate, a cardboard material, formed wood or wood pulp, or a combination thereof. Embodiments intended for a static location, for instance permanent location within an operating theatre, will benefit from the substantially impervious, anti-corrosive and hard-wearing characteristics of stainless steel and/or thermoplastics, which are moreover particularly easy to clean and sanitise. Embodiments intended for ad hoc field use, for instance at the site of a medical emergency, may instead be discarded after use for practical and sanitary reasons, wherein a cardboard material provides advantages in terms of both costs and transported weight, particularly if a recycled cardboard or other formed natural material.

According to another aspect of the present invention, there is also provided a kit of parts for a medical support structure, comprising a plurality of leg members, at least one supporting member, wherein assembly of the plurality of leg members with the at least one supporting member forms a framework having a main axis, and a top surface locatable atop the framework, adapted to support one or more refuse containers each having an aperture and a bottom portion, wherein the at least one supporting member is locatable intermediate the top surface and a lower portion of the plurality of leg members, and is adapted to support at least one medical waste container having an aperture in an upper portion thereof, wherein at least a first longitudinal portion of the supporting member forms an obtuse angle relative to a second longitudinal portion of the supporting member so as to angle the or each supported medical waste non-orthogonally relative to the top surface in use, and wherein a portion of the top surface area is recessed above the or each supported medical waste container.

As hereinbefore, embodiments of the kit of parts according to the invention may further comprise releasable securing means for securing refuse containers to the top surface, and/or a base locatable intermediate the or a lowest supporting member and the lower portion of the plurality of leg members, and/or a plurality of wheels attachable to leg members of the framework.

Any of the above embodiments may usefully be packaged in disassembled form, for self-assembly by a user, regardless of the material of manufacture of the parts. This is considered particularly useful for transportable embodiments of the structure for ad hoc deployment on a treatment site. A preferred embodiment may thus comprise a reduced number of structural components, for instance five, configured for self-assembly with one or a variety of assembling means variously including self-locating shapes, snap-fit tabs, joining clips and screw or nut and bolt fasteners. This configuration advantageously reduces the amount of welding, joints and seams required.

Other aspects are as set out in the claims herein.

BRIEF DESCRIPTION OF THE DRAWINGS

For a better understanding of the invention and to show how the same may be carried into effect, there will now be described by way of example only, specific embodiments, methods and processes according to the present invention with reference to the accompanying drawings in which.

DETAILED DESCRIPTION OF THE PREFERRED EMBODIMENT

There will now be described by way of example a specific mode contemplated by the inventors. In the following description numerous specific details are set forth in order to provide a thorough understanding. It will be apparent however, to one skilled in the art, that the present invention may be practiced without limitation to these specific details. In other instances, well known methods and structures have not been described in detail so as not to unnecessarily obscure the description.

The words "comprises/comprising" and the words "having/including" when used herein with reference to the present invention are used to specify the presence of stated features, integers, steps or components but does not preclude the presence or addition of one or more other features, integers, steps, components or groups thereof.

Figure 1:
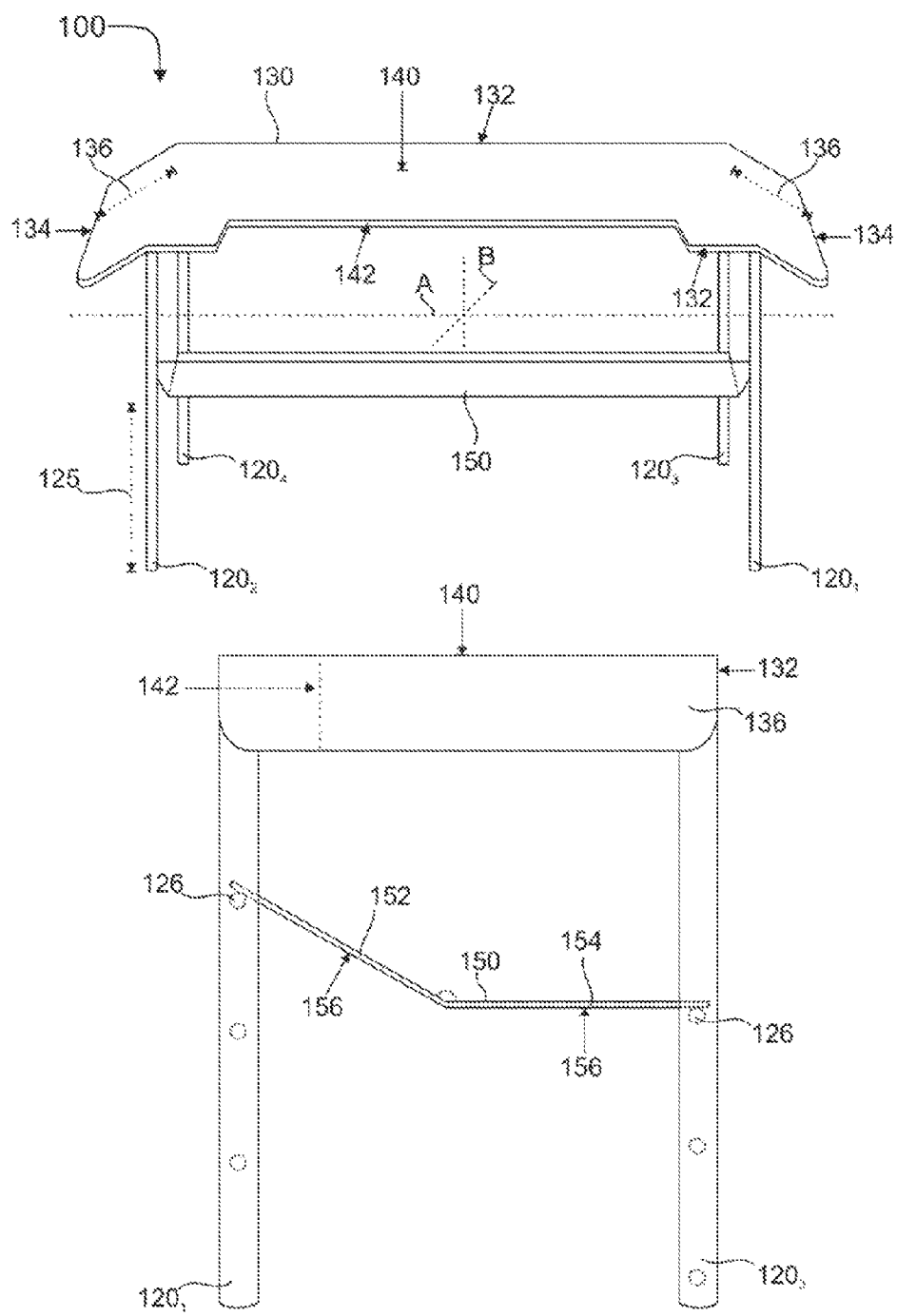
FIG. 1 shows both a perspective view and an end view of a first embodiment of a medical structure according to the invention, comprising a framework, leg members and a supporting member.

Referring now to the Figures, there is shown a first embodiment of a medical support structure 100 according to the invention is shown in FIG. 1, which comprises a framework 110 having a main axis A and a transverse axis B (both shown in dotted line) and a plurality of substantially rectilinear, elongate leg members $120_{1-4}$. The structure 100 further comprises a substantially planar member 130 having a top surface 140, and locatable atop the framework 110. The structure 100 further comprises a supporting member 150 located intermediate the upper member 130 and a lower portion 125 of each of the plurality of leg members $120_{1-4}$.

In this embodiment, the upper member 130 is substantially rectangular, having parallel sides 132 that are longer in a direction parallel to the main axis A of the structure 100, and parallel ends 134 which are shorter than, and orthogonal to, the parallel sides 132. Adjacent each end 134, a portion 136 of the upper member 130 is angled downwardly relative to the main horizontal portion of the top surface 140, which main portion is orthogonal to, and extends substantially between, longitudinally-opposed leg members $120_{1-2}$ ($120_{3-4}$). Accordingly, each portion 136 of the upper member 130 defines a downwardly-angled flange or winglet 136 such that the upper member 130 has a longitudinal profile shaped substantially like an inverted U with a flattened midsection.

The supporting member 150 has a length corresponding substantially to the distance between longitudinally-aligned leg members $120_{1-2}$ ($120_{3-4}$), and a width corresponding substantially to the distance between transversally-aligned leg members $120_{1-3}$ ($120_{2-4}$). The supporting member 150 is substantially rectangular in top view. In a transverse end view, however, a first longitudinal portion 152 of the supporting member 150, corresponding in this embodiment to a first longitudinal half thereof, forms an obtuse angle α relative to a second longitudinal portion 154, corresponding to the second longitudinal half thereof, such that the supporting member 150 has a transverse profile substantially like a V.

The top surface of the second longitudinal portion 154 of the supporting member 150 is substantially parallel to the main horizontal portion of the top surface 140, and a portion 142 of the top surface area 140 of the upper member 130 is recessed directly above the first longitudinal portion 152 of the supporting member 150, wherein the recessed portion 142 is substantially centred relative to the transverse axis B of the upper member 130.

The supporting member 150 is maintained in position intermediate the upper member 130 and the lower portion 125 of the leg members $120_{1-4}$ with relevant support and/or fastening means, in the example a plurality of support pins 126 extending from the surface of each of the plurality of leg members $120_{1-4}$ towards the geometrical centre of the structure and parallel to its mains axis, wherein the underside 156 of the supporting member 150 comes to rest upon the pins 126.

In alternative embodiments, the support pins 126 may be substituted for longitudinal support bars of a diameter substantially identical to the pins 126 and extending between longitudinally-aligned leg members $120_{1-2}$ ($120_{3-4}$) in parallel to the main axis of the support structure, providing increased stability to the support member 150 resting thereon and increased structural integrity to the whole structure 100.

Figure 9A:
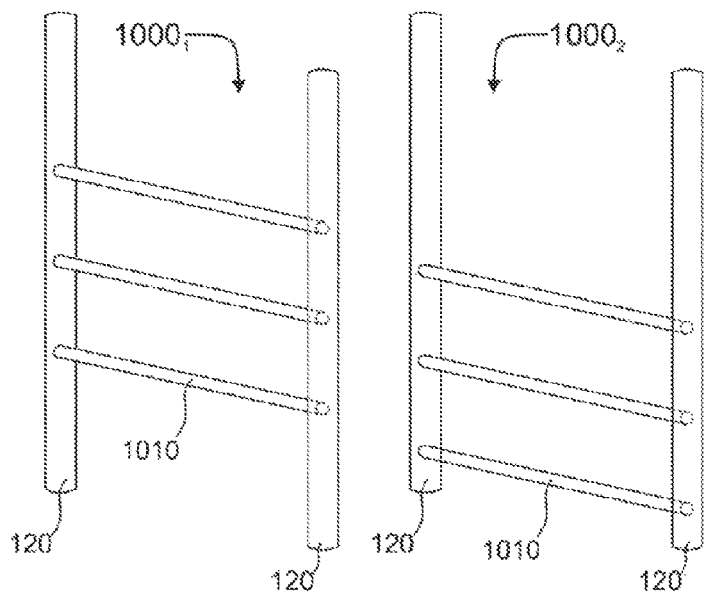
FIGS. 9A and 9B shows perspective views of framework members comprising substantially H-shaped substructures for use with self-assembly embodiments of the medical structure according to the invention.

In a simple form of this alternative embodiment shown in FIG. 9A, the lower portion of the structure 100 underneath the top member 130 effectively takes the form of two substantially H-shaped substructures $1000_1$, $1000_2$, each comprising two leg members 120 joined by a plurality of longitudinal support bars 1010 parallel to one another and orthogonal to the main axis of the leg members, with the support bars 1010 of one substructure $1000_1$ transversely offset relative to the support bars 1010 of the opposed substructure $1000_2$ so as to accommodate the angled transverse profile of any support member 150 resting thereon.

Figure 9B:
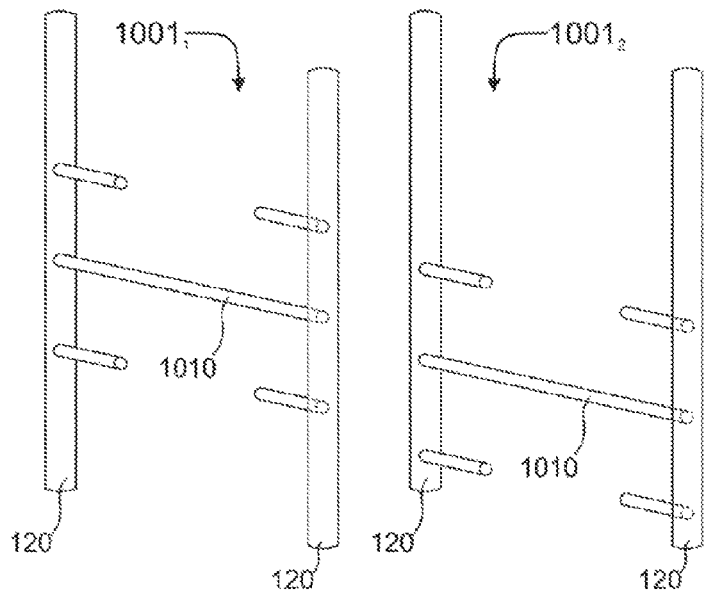

In another, still simpler form of this alternative embodiment shown in FIG. 9B, the lower portion takes the same form of two substantially H-shaped substructures $1001_1$, $1001_2$, each again comprising two leg members 120 joined by a single longitudinal support bar 1010, and support pins 126 as previously described instead of parallel bars 1010, advantageously reducing materials use and weight.

Figure 2:
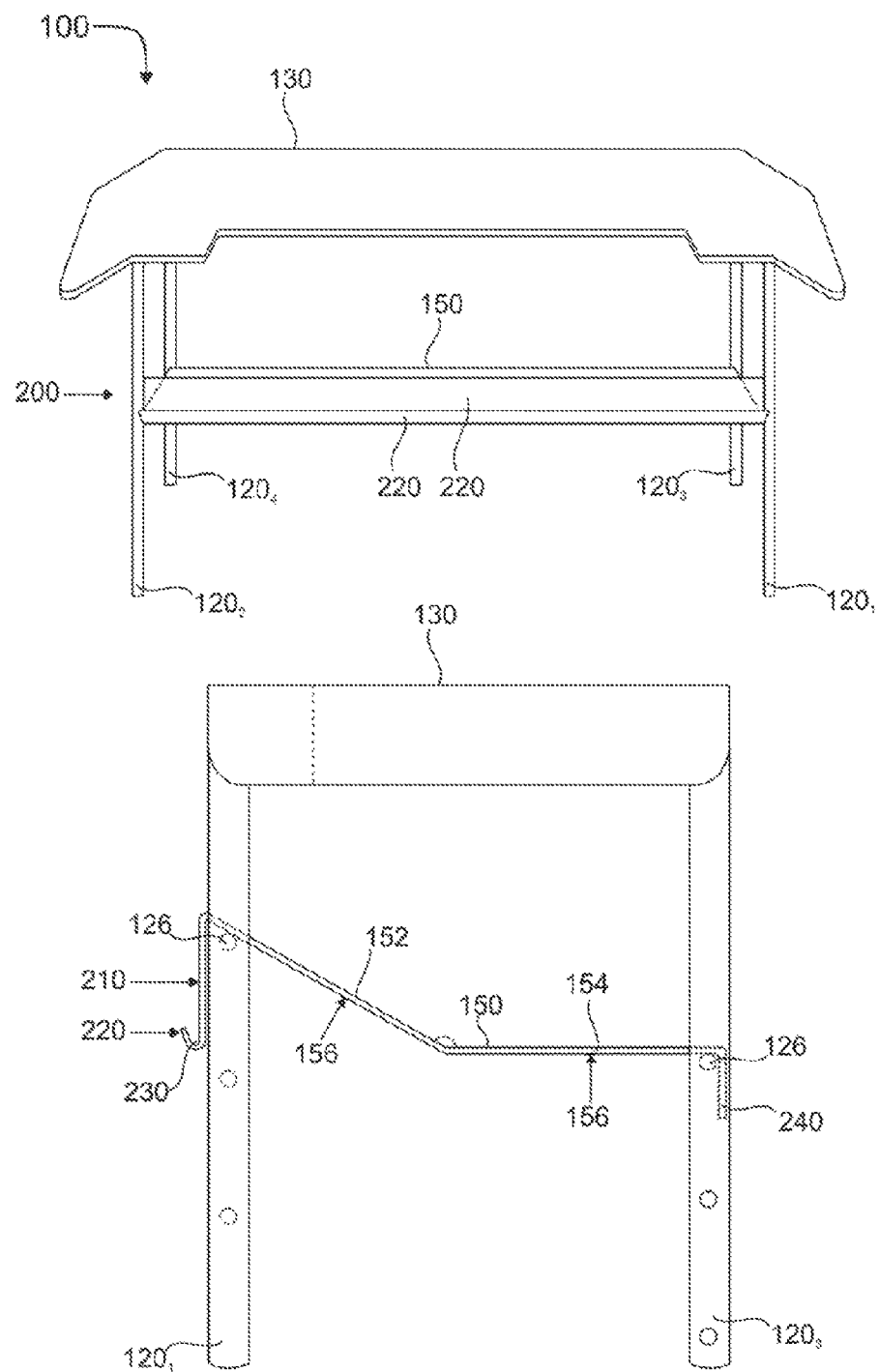
FIG. 2 shows both a perspective view and an end view of the medical structure of FIG. 1, with an alternative embodiment of a supporting member having a drip tray.

In an alternative embodiment of the structure shown in FIG. 2, in which like features are designated with like reference numerals, the supporting member 150 further comprises a drip tray 200 extending along its periphery on the side of the first longitudinal portion 152 distal the second longitudinal portion 154.

The drip tray 200 consists of a portion 210 of the first longitudinal section 152, which is longitudinally folded relative to its angled top surface so as to form an angle of substantially 90 degrees relative to the top surface of the second longitudinal section 154, thus forming an acute angle relative to the surface of the underside 156, then longitudinally counter-folded proximate the outermost edge 220 of longitudinal section 152 so as to form a longitudinal channel 230 between the vertical portion 210 and the edge 220.

Opposed to the drip tray 200, the supporting member 150 further comprises a locating flange 240 extending along its periphery on the side of the second longitudinal portion 154 distal the first longitudinal portion 152.

The locating flange 240 consists of a portion 240 of the second longitudinal section 154, which is longitudinally folded relative to its top surface so as to form an angle of substantially 90 degrees relative to the top surface of the second longitudinal section 154, thus forming an acute angle relative to the surface of the underside 156. In combination with the drip tray 200, this configuration of the longitudinal sides of the support member 150 facilitate its transverse positioning relative to asymmetrically-opposed pins 126 of opposed leg members 120 and, once the support member 150 is resting on the support pin 126, results in a transverse structural strengthening of the framework underneath the planar member 130.

Figure 3:
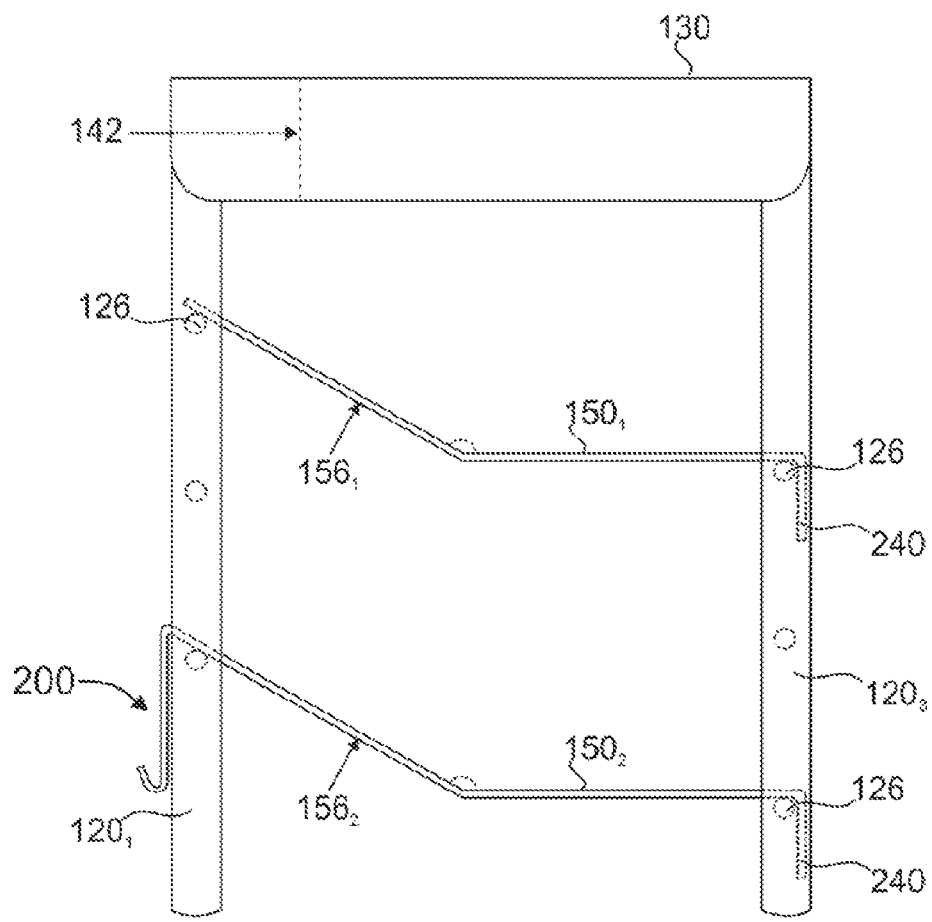
FIG. 3 shows an end view of the medical structure of FIGS. 1 and 2, with two supporting members in superimposition.

With reference to FIG. 3, several support members 150 each according to a respective embodiment, i.e. including a front drip tray 200 and/or a rear locating flange 240, may be used in combination with a same support structure 100, according to medical refuse streaming requirements of any or all of the practitioner, the procedure and the location of use.

Figure 4A:
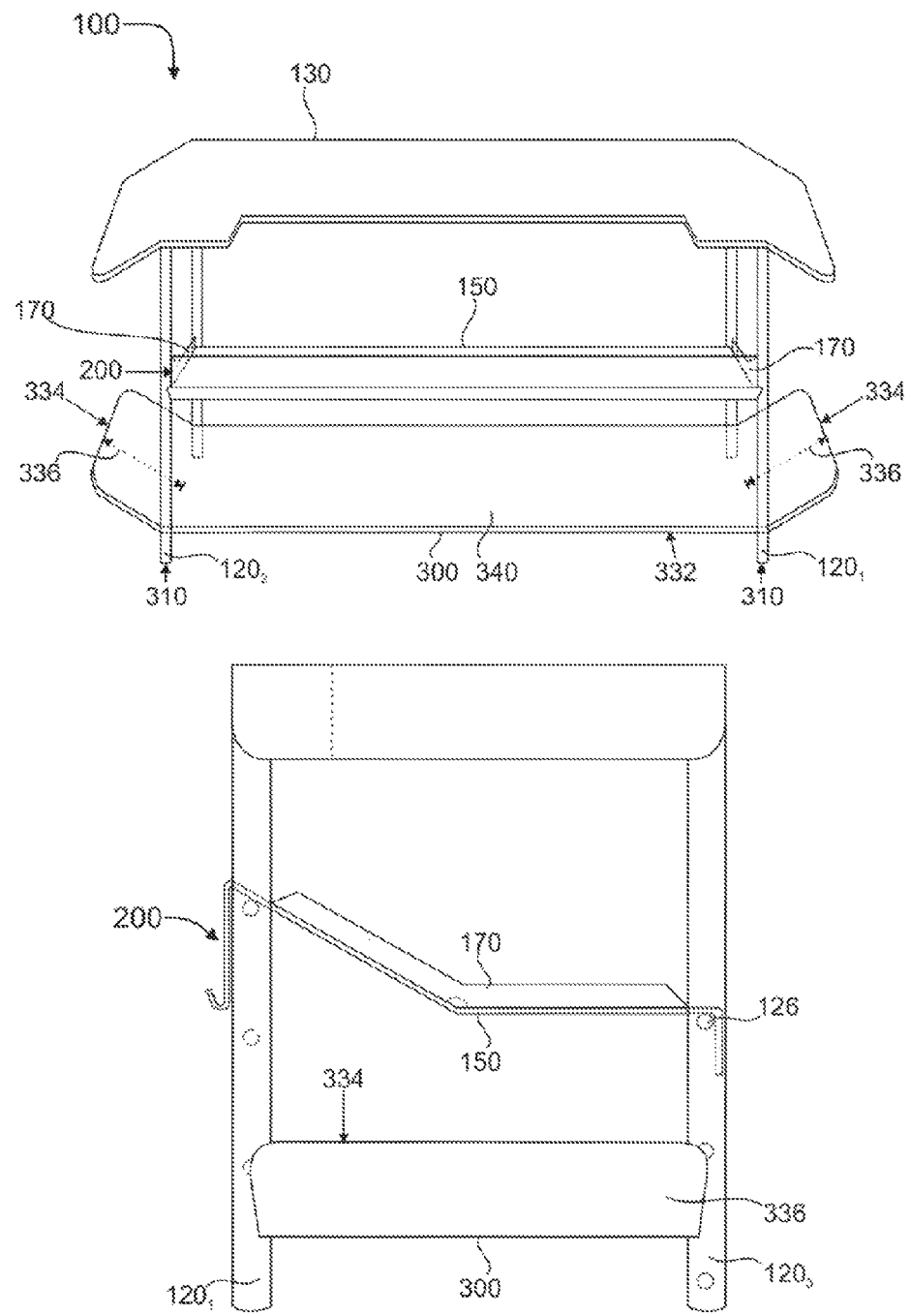
FIG. 4A shows both a perspective view and an end view of a second embodiment of a medical structure according to the invention, comprising a base member and yet another embodiment of a supporting member having end flanges.

In an alternative embodiment shown in FIG. 4A, in which like features are designated with like reference numerals, the structure 100 further comprises a base member 300 located intermediate the supporting member 150 and the lowest extremity 310 of each of the plurality of leg members $120_{1-4}$. The base member 300 is substantially rectangular, having parallel sides 332 that are longer in a direction parallel to the main axis A of the structure 100, and parallel ends 334 which are shorter than, and orthogonal to, the parallel sides 332.

Adjacent each end 334 of the base member 300, a portion 336 of the base member 300 is angled upwardly relative to the main horizontal portion of the top surface 340 of the base member, which is orthogonal to, and extends substantially between, longitudinally-opposed leg members $120_{1-2\ (3-4)}$. Accordingly, each portion 336 of the base member 300 defines an upwardly-angled flange 336 such that the base member 300 has a longitudinal profile shaped substantially like a U with a flattened mid-section.

Also shown in FIG. 4A is a further embodiment of the supporting member 150, having end flanges 170, each of which extends orthogonally to the top surface of each supporting member longitudinal portion 152, 154 and has a total length approximately equal to the distance between transversally-opposed leg members $120_{1-3}$ ($120_{2-4}$). The flanges 170 are accordingly provided at the longitudinally-opposed ends of the supporting member 150 and prevent any medical waste container located thereon from accidentally rolling beyond and falling from the supporting member 150 along a longitudinal direction.

Figure 4B:
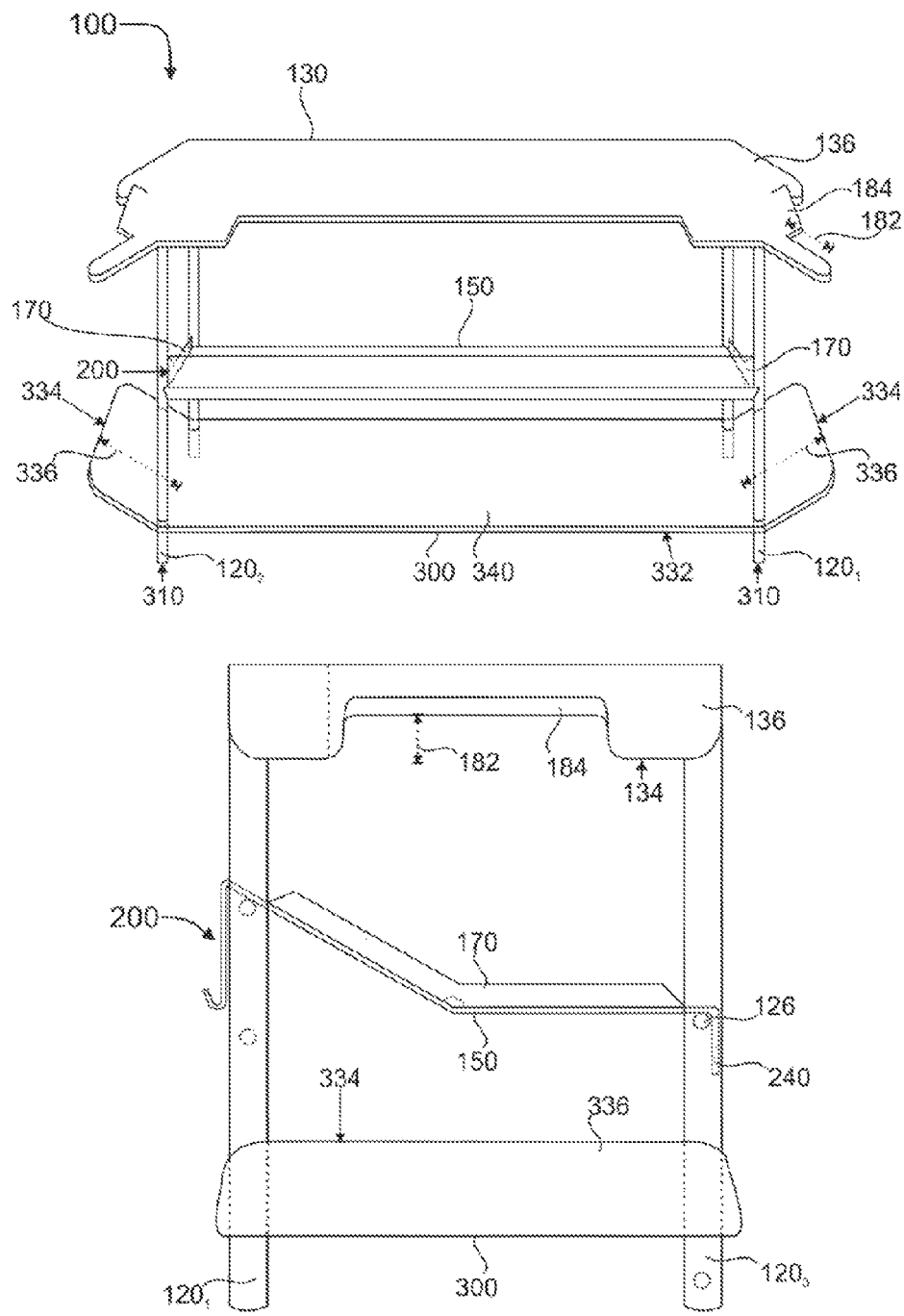
FIG. 4B shows both a perspective view and an end view of a third embodiment of a medical structure according to the invention, comprising alternative planar and base members, with the base member having a width exceeding the transverse distance between leg members.

In an alternative embodiment shown in FIG. 4B, in which like features are designated with like reference numerals, the length of each parallel end 334 exceeds the distance between transversally-opposed leg members $120_{1-3}$ ($120_{2-4}$), such that the parallel sides 332 of the base member are proud of the substantially vertical plane defined by longitudinally-opposed leg members $120_{1-2}$ ($120_{2-4}$), wherein all four leg members are journaled through the main horizontal portion of the top surface 340 of the base member 300. This configuration advantageously hinders a fall to the floor of any liquid accidentally spilled from the top surface 140 and/or from a medical waste container supported on the support member 150 and/or past the drip tray 200.

Also shown in FIG. 4B is an alternative embodiment of the top member 130, wherein a first transverse and elongate portion 182 of each flange 136 is recessed a short distance from the end 134 into the flange 136, between the transversely-opposed rounded corners of the planar member 130 and substantially centred relative to the main axis A, and wherein a second transverse and elongate portion 184 of each flange 136 along the length of the recessed portion 182 forms a transverse lip standing upward of the substantially planar surface of the flange 136.

Accordingly, each transverse lip 184 of the upper member 130 defines an upwardly-angled transverse flange or winglet 184 having a shorter transverse dimension than the upwardly-angled flange or winglet 136. This configuration advantageously hinders uncontrolled spillage or rolling of liquids, materials and objects down the flange 136 into a refuse container supported thereon as described hereafter, whilst providing an anchoring surface to help support the said refuse container thereon, again as described hereafter.

Figure 5A:
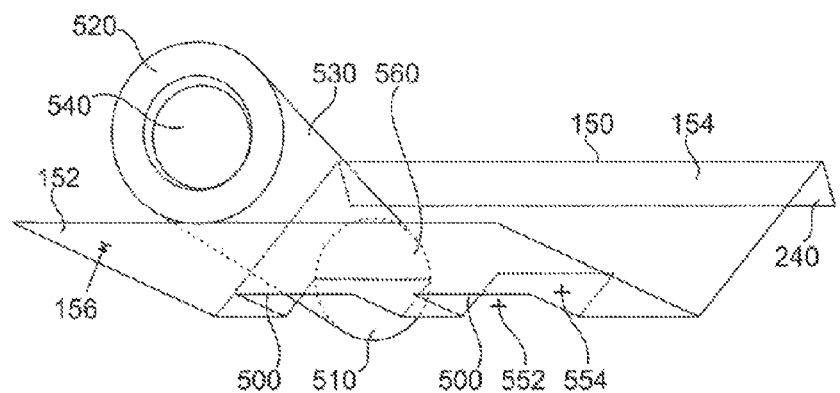
FIG. 5A shows a perspective view of another embodiment of the supporting member, comprising a plurality of lodgements for respective containers.

In an alternative embodiment of the supporting member 150 shown in FIG. 5A, in which like features are designated with like reference numerals, the supporting member 150 further comprises a plurality of lodgements 500 for accommodating a lower portion 510 of a medical waste container 520 therein, when the medical waste container 520 is otherwise rested upon the first longitudinal portion 152 of the support member 150 by its lateral wall 530, such that its aperture 540 is angled upwards but not orthogonally to the upper member top surface 140.

In the embodiment shown, each lodgement 500 is a substantially square through-aperture 500 spanning a portion 552 of the first longitudinal half 152 and a transversally-aligned portion 554 of the second longitudinal portion 154. Accordingly, in use, as a medical waste container 520 is rested upon the top surface of the first longitudinal portion 152 in alignment with a lodgement 500, then slid towards the lodgement, a bottom portion 510 of the medical waste container 520 passes through the lodgement and underneath the underside 156 of the supporting member 150, and the bottom surface 560 of the medical waste container 520 abuts the longitudinal edge of the lodgement 500 on the second longitudinal portion 154, with the parallel edges of the lodgement 500 orthogonal to that longitudinal edge maintaining the body of the medical waste container 520 in position.

Figure 5B:
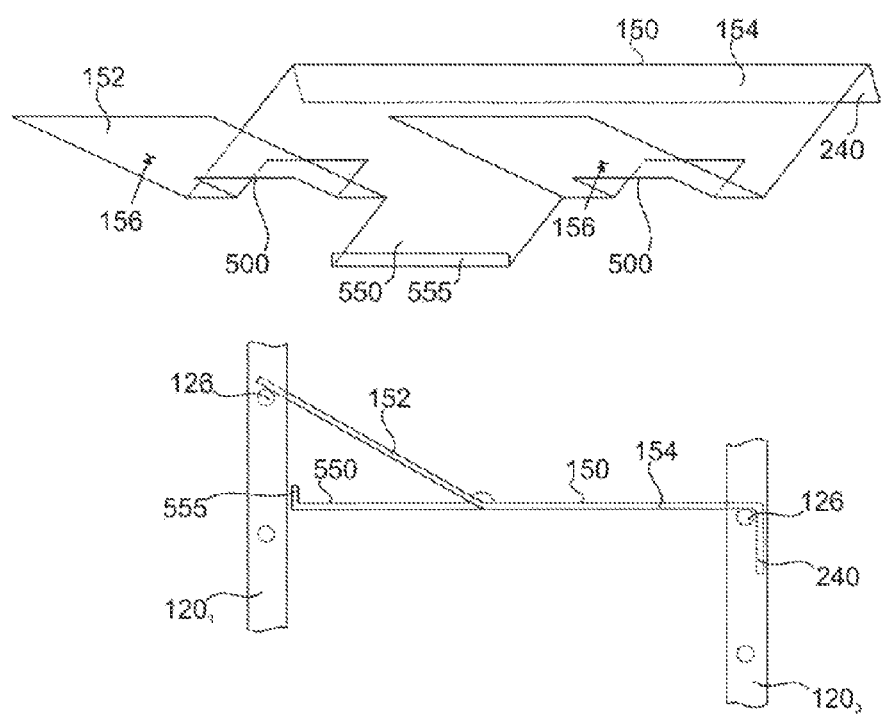
FIG. 5B shows both a perspective view and an end view of yet another embodiment of the supporting member, comprising the plurality of lodgements for respective containers of FIG. 5A and a planar section for resting medical and/or monitoring equipment.

In an alternative embodiment of the supporting member 150 shown in FIG. 5B, in which like features are designated with like reference numerals, the supporting member 150 further comprises a planar section 550 intermediate a pair of lodgements 500 for supporting medical and/or monitoring equipment, for instance an electrocardiogram (ECG) unit, a heart rate monitoring device, a blood pressure monitoring device, or the like, typically in frequent use during a medical procedure and the location of which underneath the top member 130 may be preferred for passive protection against knocking, spillages and more.

The planar section 550 consists for instance of a portion of the first longitudinal portion 152 maintained in planar alignment with the opposed second longitudinal portion 154 across the median axis along which both portions form an angle, wherein distally opposed portions of the first longitudinal portion 152, one on each side of the planar section 550 and each with sufficient dimensions to include a lodgement 500, form the said obtuse angle α relative to the second longitudinal portion 154, such that this embodiment of the support member remains compatible with the support pins 126 or bar(s) 1010. The extremity 555 of the planar section 550 distal the second longitudinal portion 154 is preferably folded longitudinally upwards relative to its top surface so as to form a peripheral lip 555 with an angle of substantially 90 degrees relative to the top surface of the planar section 550, which assists in preventing an accidental fall of any medical and/or monitoring equipment supported thereon.

The supporting member 150 may further comprise cabling management means for the medical and/or monitoring equipment supported on the planar section 550. The cabling management helps prevents entanglement of equipment wiring with snagging hazards on and adjacent the support structure 100 and also helps to shield such cabling or wiring from spillages and projections of hazardous waste. Accordingly, in an alternative embodiment of the supporting member 150 shown in FIG. 5C, in which like features are designated with like reference numerals, a pair of longitudinally-opposed cable guides 570 is provided, with one guide 570 adjacent each longitudinal extremity of the second longitudinal portion 154. Each guide 570 consists of a box-like open housing, having two walls extending upwards from the top surface of the second longitudinal portion 154 at a distance from each other, and joined at their respective extremities distal the second longitudinal portion 154 by a top wall, such that a through-aperture is defined between the top surface of the second longitudinal portion 154, the two side walls and the tope wall. Cabling 575 for any equipment (not shown) supported on the planar section 555 can be passed therethrough, such that any accidental stretching or pulling of the cable 575 through motion of the equipment or structure 100 relative to a remote socket is mitigated by the guiding constraint 570.

Figure 5C:
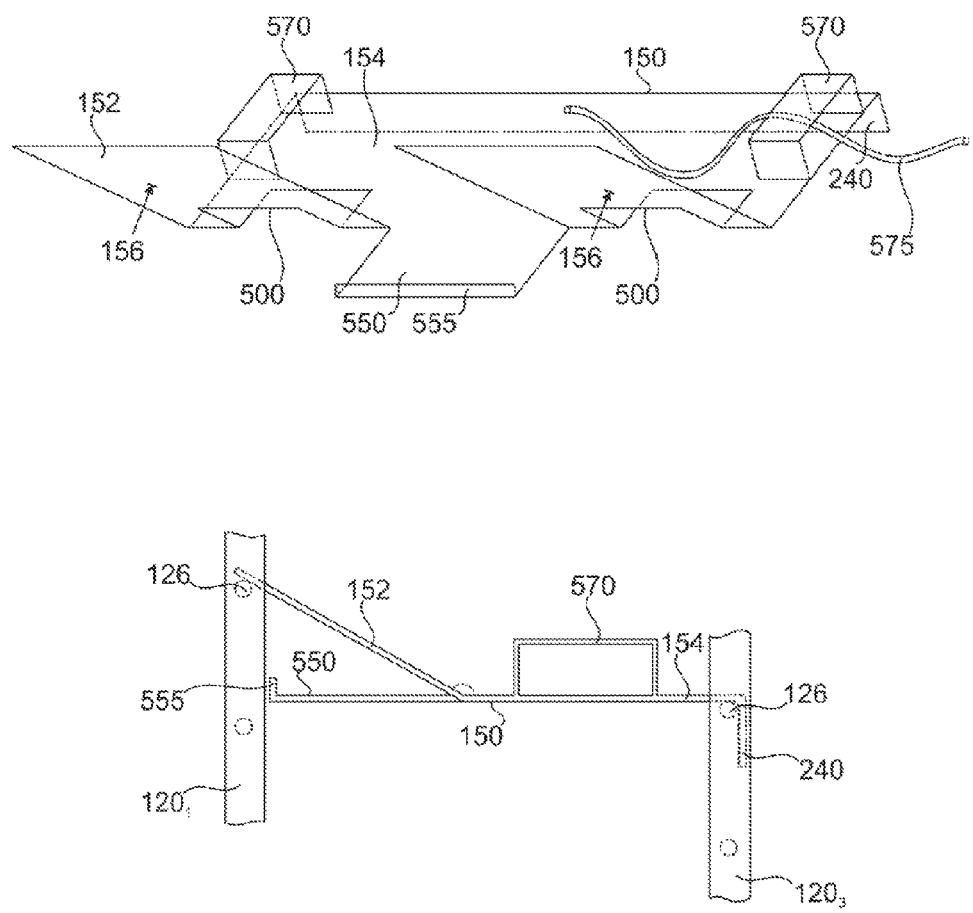
FIG. 5C shows both a perspective view and an end view of another embodiment of the supporting member of FIG. 5B, with end flanges as shown in FIG. 4A having apertures for passing medical and/or monitoring equipment wiring therethrough.

It will be readily understood by the skilled person that the embodiments shown and described in FIGS. 5A, 5B and 5C are provided herein by way of non-limitative example, and may be still more varied in aspects of shape and configuration and/or combined. For instance, the end flanges 170 of FIGS. 4A and 4B may be combined with the longitudinally-opposed cable guides 570 of FIG. 5C, with having the flange 170 extending from the side wall on either side of the through-aperture 570.

Figure 6:
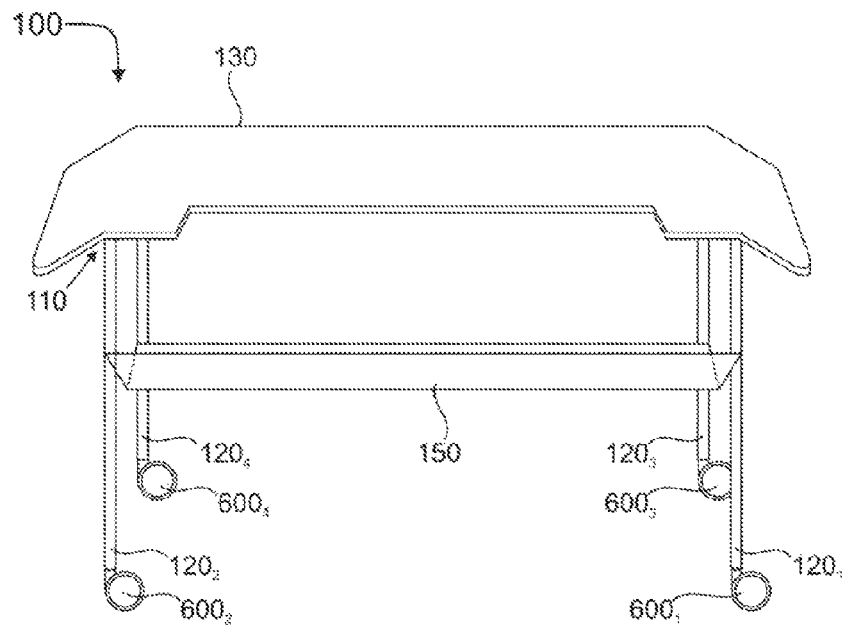
FIG. 6 shows a perspective view of a fourth embodiment of the medical structure comprising wheels.

In a further alternative embodiment shown in FIG. 6, in which like features are designated with like reference numeral, the structure 100 further comprises a plurality of antistatic wheels 600$_N$, wherein each wheel 600 is securely fastened to the underside 310 of a respective leg member 120$_{1-4}$, for instance through a push-fit engagement which maintains the wheel assembly captive but allows free orientation of the rotational axis of the wheel 600 about the main axis of a leg member 120$_N$.

Figure 7:
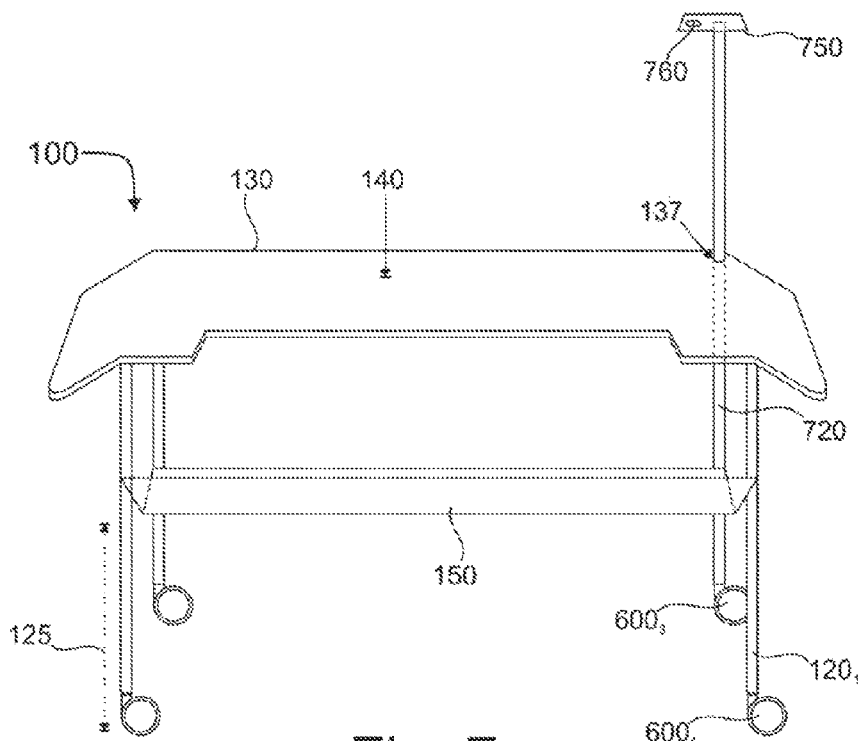
FIG. 7 shows a perspective view of a fifth embodiment of the medical structure with at least one leg member projecting above the top surface.

In an alternative embodiment shown in FIG. 7, in which like features are designated with like reference numerals, one leg member 720 extends upwardly through a corresponding through-aperture 137 in the upper member 130 and the top surface 140 thereof above the top surface 140. The extremity of the elongated leg member 720 distal the lower portion 125 thereof is provided with a mounting plate 750 having at least one through-aperture 760 off-centred relative to the cross-sectional dimension of the elongated leg member 720, as a mounting point for any medical or non-medical device, apparatus or container. The extremity of the elongated leg member 720 distal the lower portion 125 of same is specifically not provided with a blind mounting hole or the like within the cross-sectional dimension of the elongated led member 720, to avoid harbouring any dust, bacteriological waste or other contaminant which would prove difficult to clean therein.

Figure 8A:
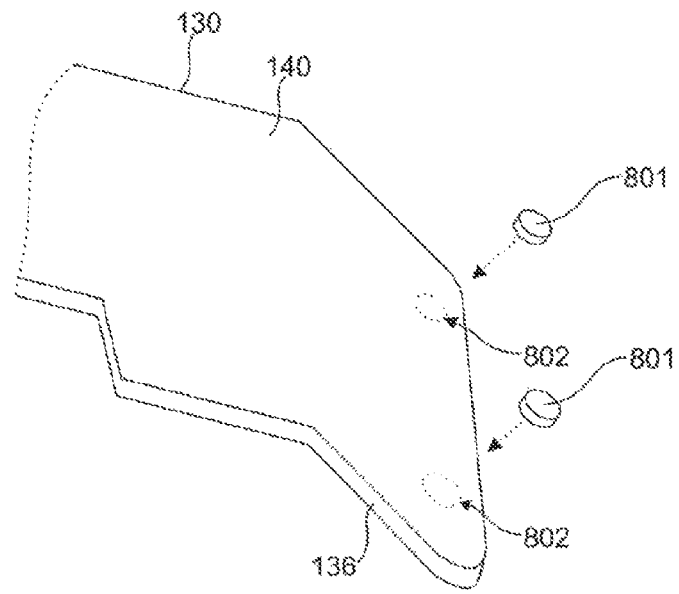
FIGS. 8A and 8B illustrate releasable securing means suitable for various embodiments of the medical structure.
Figure 8B:
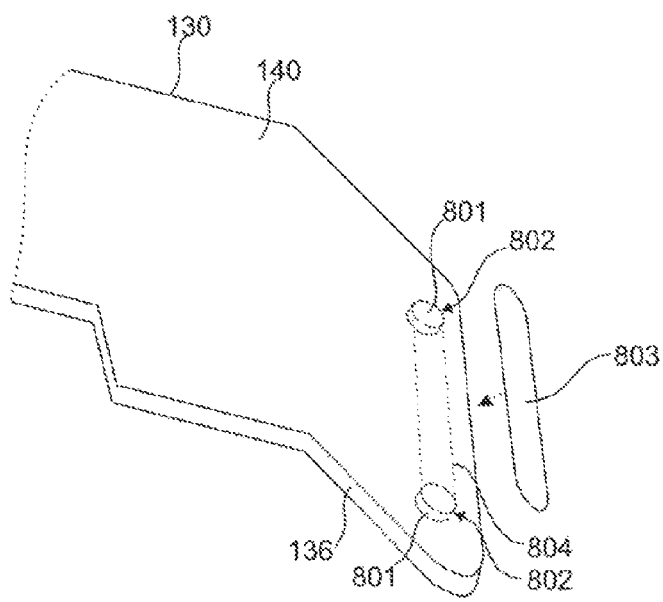
Figure 8C:
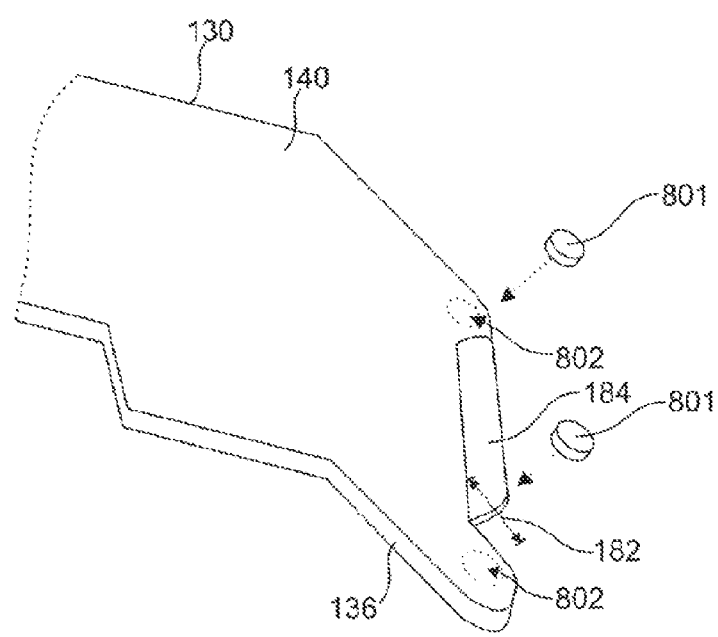
FIG. 8C illustrate releasable securing means with the alternative planar member of FIG. 4B.
Figure 8C:
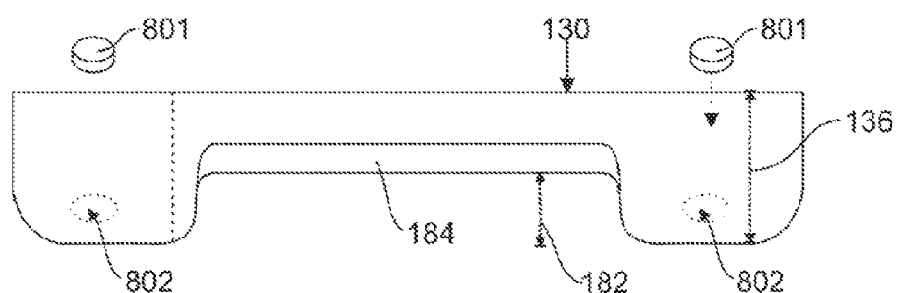

Embodiments of releasable securing means are respectively shown in FIGS. 8A, 8B and 8C for securing a soft form refuse container such as a refuse bag atop the top surface 140 of one or both flange portions 136 of planar member 130.

In a first embodiment shown in FIG. 8A, the releasable securing means takes the form of two magnets 801, which are releasable from respective positions 802 on the top surface 140 adjacent the or each end 134 of the planar member 130, when the top surface 140 or at least portions thereof corresponding at least to the respective positions 802 is made of a ferrous or other magnetic material.

When released, by overcoming the magnetic force which attracts the magnets 801 to the top surface 140 and reciprocally, a portion of the wall of a refuse container can be abutted atop and cover a portion of the top surface 140 corresponding to at least a portion of the flange 136 including the said positions 802, and the magnets 801 are then magnetically adhered back to the said positions 802 and hold the portion of refuse container wall captive thereagainst in use. The two positions 802 and magnets 801 are aligned substantially parallel to the transverse axis of the structure, thus parallel to the planar member end 134, at a distance which ensures that the top opening of a soft form refuse bag is maintained at least partially opened as a consequence of gravity upon the refuse bag and its soft form material, typically a plastic film.

The embodiment based on two releasable magnets 801 is considered compatible with most embodiments of the top member 130, including for instance that shown in FIG. 4B wherein the first transverse and elongate portion 182 of each flange 136 is recessed a short distance from the end 134 into the flange 136, and a second transverse and elongate portion 184 forms a transverse lip standing upward of the substantially planar surface of the flange 136, and wherein the respective magnet positions 802 are located on either side of the elongate recessed portion 182, as shown in FIG. 8C.

In a second embodiment shown in FIG. 8B, the releasable securing means again comprises two magnets 801, which in this embodiment here embedded at respective positions 802 within the material constituting the or each flange portion 136 of the planar member 130 adjacent its end 134, and have an upper surface coincident with or, if fully embedded within the member material, then closely adjacent, the top surface 140. In this embodiment, the releasable securing means further comprises a securing flat iron or bar 803 made from a ferrous or other magnetic material, which extends over at least the two embedded magnets 801 and a linear distance therebetween (shown at 804), and is releasable therefrom by overcoming the magnetic force which attracts the bar 803 to the magnets 801 and reciprocally.

When the bar 803 is released, a portion of the wall of a refuse container can again be abutted atop and cover a portion of the top surface 140 corresponding to at least a portion of the flange 136 including the embedded magnets 801, and the bar 803 is then magnetically adhered back to the said magnets 801 and holds the portion of refuse container wall captive thereagainst in use. The magnets 801 are again aligned substantially parallel to the transverse axis of the structure, thus parallel to the planar member end 134, and the corresponding length of the bar 803 ensures that the top opening of a soft form refuse bag is again maintained at least partially opened as a consequence of gravity upon the refuse bag and its soft form material. For a structure of stainless construction with insubstantial magnetic properties, disposable clips made of plastic, metal, wood or another inexpensive and inert material may be used to temporarily secure the refuse container to the structure.

Figure 12A:
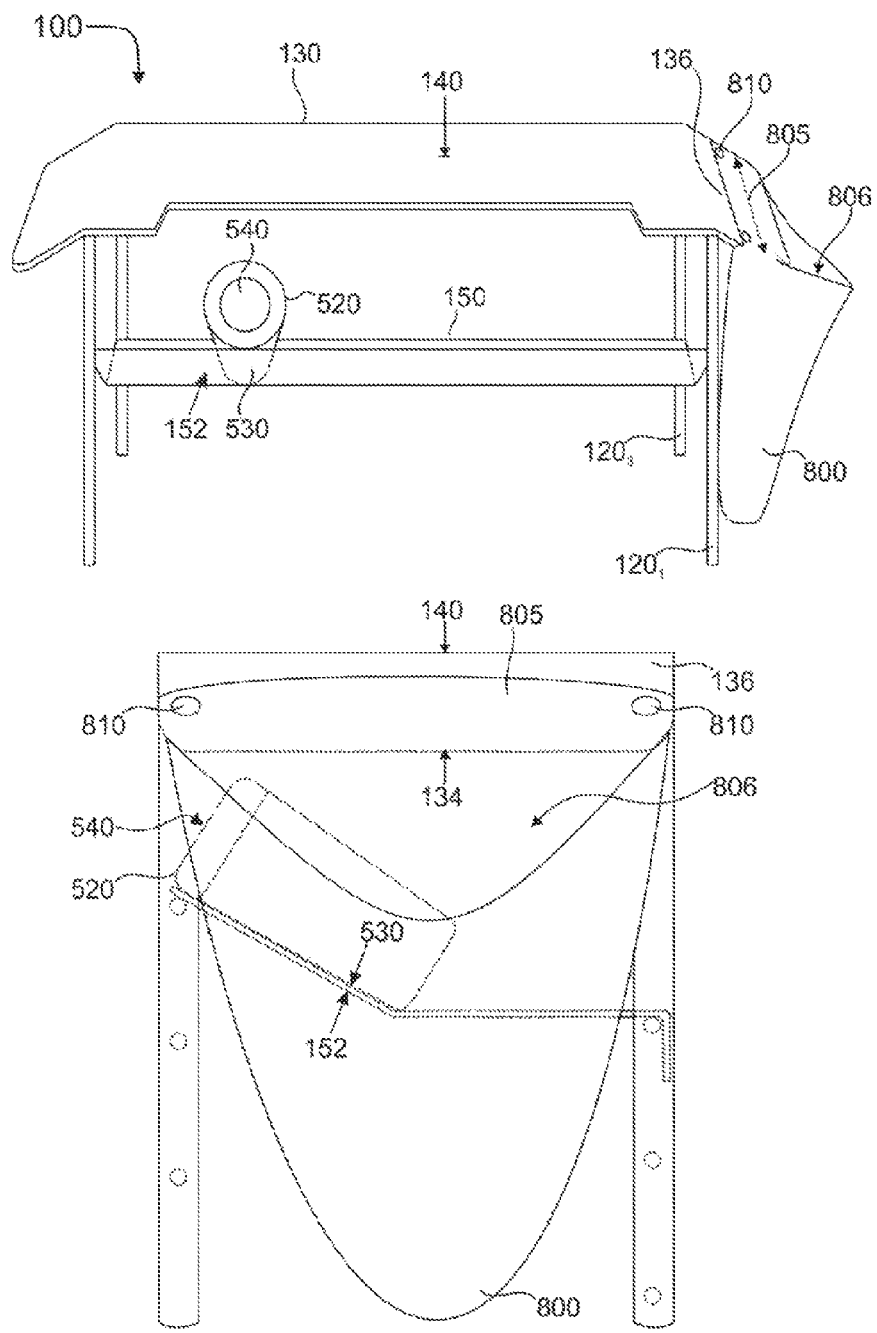
FIG. 12A shows the medical structure of FIG. 1 supporting both a soft form refuse container and a medical waste container in use.

With reference to FIG. 12A now, the embodiment of the structure 100 described with reference to FIG. 1 and comprising a top member 130 with downturned flanges 136 and a supporting member 150 with a locating flange 240 is shown in use, with a medical waste container 520 supported by the supporting member 150 and a refuse container 800 supported by one of the downturned flanges 136.

The medical waste container 520 is rested upon the first longitudinal portion 152 of the support member 150 by its lateral wall 530, such that its aperture 540 is angled upwards but not orthogonally to the top surface 140 of the top member 130. An upper portion 805 of the lateral wall of the refuse container 800 adjacent its top aperture 806 is abutted to the top surface 140 of the downturned flange 136 and held in place with magnets 810, such that the container is maintained in a generally upright stance with its aperture 806 held open by the exercise of gravity upon the rest of the lateral wall of the refuse container 800 on either side of the upper portion 805, and particularly upon the upper portion of the lateral wall opposed to the secured portion 805.

Figure 12B:
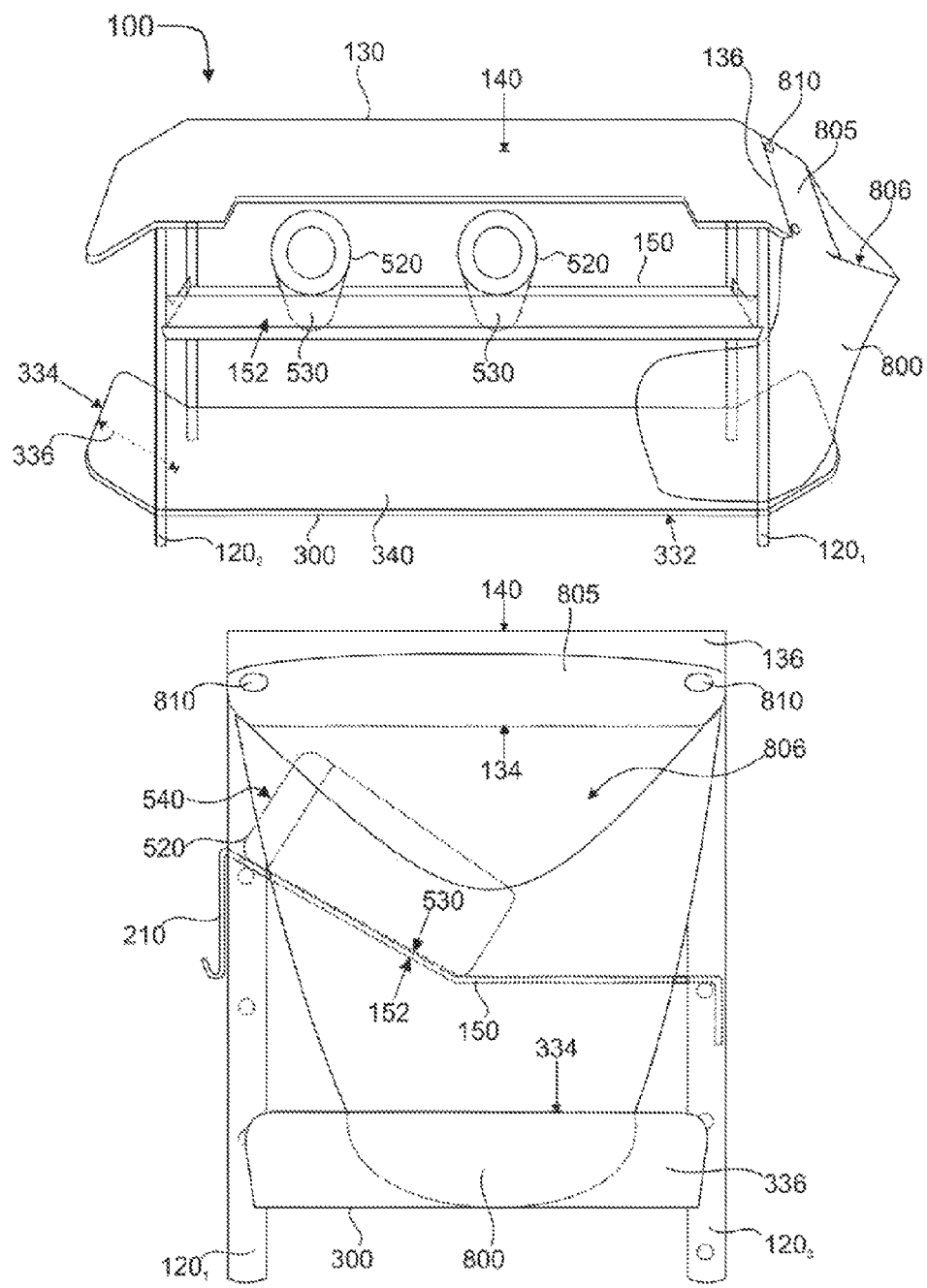
FIG. 12B shows the medical structure of FIG. 3 supporting both a soft form refuse container and a plurality of medical waste containers in use.

With reference to FIG. 12B now, the embodiment of the structure 100 described with reference to FIG. 4A and comprising a top member 130 with downturned flanges 136, a supporting member 150 with a locating flange 240, a drip tray 200 and end flanges 17, and a base member 300 with upturned flanges 336 is shown in use, with a pair of medical waste containers 520 supported side by side by the supporting member 150 and a refuse container 800 supported by one of the downturned flanges 136 and the base member 300 and protected by the upturned flange 336 thereof.

In this embodiment, the refuse container 800 is again secured to the downturned flange 136 by magnets 810, but it is supported both at its upper end by the downturned flange 136, and at its lower end by resting at least partially upon the intermediate planar portion 340 of the base 300 and leaning at least partially against the adjacent upturned flange 336. In this embodiment therefore, the portion of the soft from refuse container 800 leaning against the upturned flange 336 is usefully protected against shock or puncture vectors, which impact the material of the underside of the upturned flange 336 rather than the container 800.

The present invention accordingly provides a medical structure with an improved ergonomic configuration for contactless disposal of refuse and contaminated medical waste, which assist in maintaining sterile conditions. In all embodiments, the structure provides a work surface to assist with medical and clinical procedures and is adapted by its features to at least support both refuse containers and medical waste containers, and to protect the said medical waste containers. Embodiments of the structure can however include features favouring a high mobility in use, for use at different sites in e.g. a hospital environment for varying secondary purposes.

Other embodiments of the structure can include features favouring a high modularity, wherein either additional support members 150 can be disposed underneath the top member 130; and/or the top member 130 of FIGS. 1 and 2 can be replaced by another 130 with a through-aperture and one leg replaced with an elongate leg having a top mounting plate as shown in FIG. 7; and/or fixed-length leg members 120 can be substituted for adjustable variable length leg members, or heightened with the adjunction of spacer members intermediate the top of a fixed-length leg member 120 and the top member 130 to increase the overall height of the structure 100 and reciprocally.

Further, the underside of the top member 130 may be manufactured with blind apertures that are prepositioned proximate each corner of the substantially planar section of the top member, adjacent the end of each angled flange 136 distal its extremity 134, wherein each blind aperture is dimensioned and shaped complementarily with the highest extremity of a leg member $120_N$ opposed to its lowest extremity 310, suitable to achieve a sliding fit of the highest extremity therein.

Figure 11:
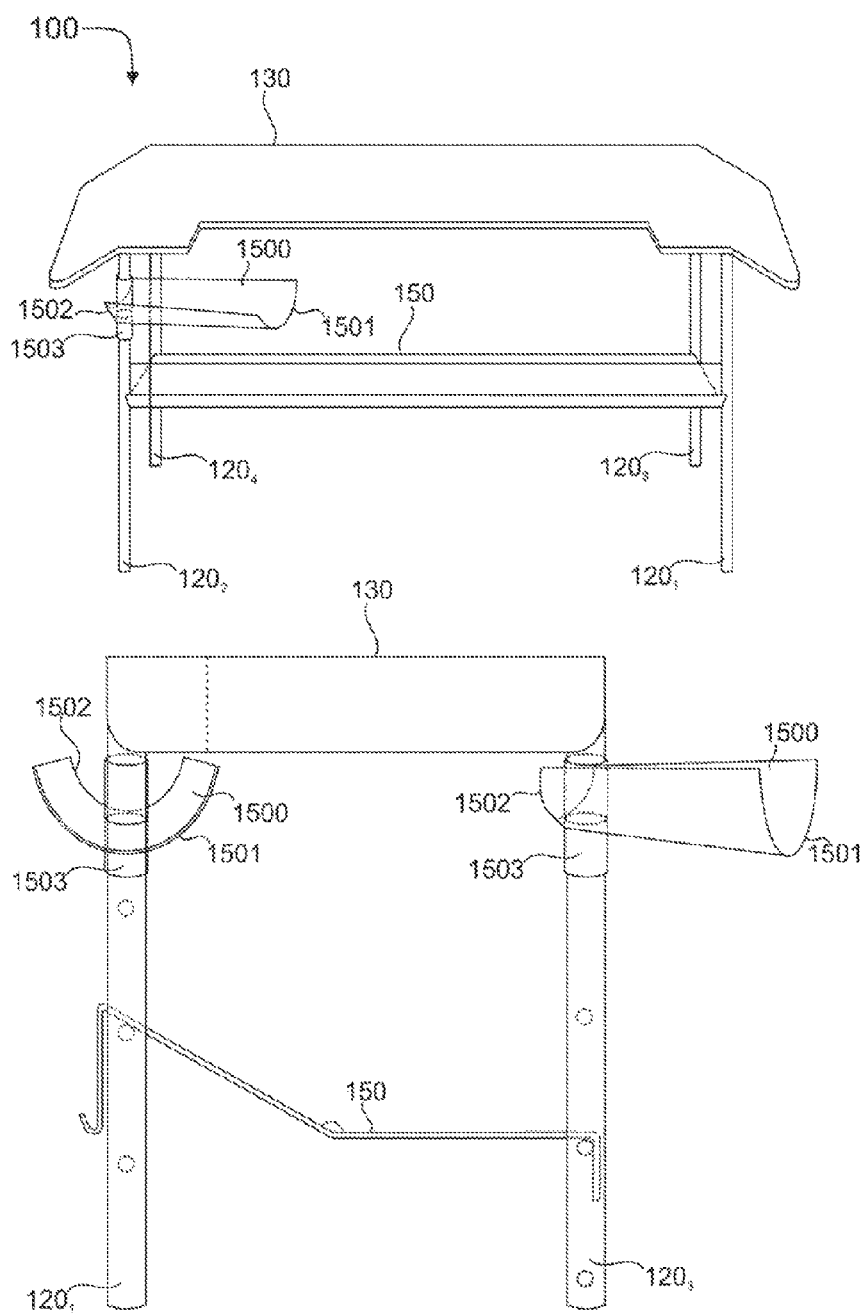
FIG. 11 shows both a perspective view and an end view of a further embodiment of a medical structure according to the invention, comprising resting members pivoted about leg members.

Further still, other types of purpose-specific support features may be adjoined to the structure 100 and/or to its framework 110, particularly in contextual association with procedures that typically involve the streaming and disposal of hazardous waste into medical waste containers 520. An example embodiment of such a purpose-specific support feature is shown in FIG. 11 as a patient arm support member 1500. The patient arm support member 1500 is an elongate and transversely arcuate member with an open longitudinal top section, having an open end 1501 distal the structure 100 and an opposed end 1502 secured to a pivoting mechanism about a leg member 120 of the framework 110, in the example a tubular sleeve 1503 secured in height to the leg member 120 but free to rotate thereabout. The patient arm support member 1500 has a constant or receding diameter between its free end 1501 and its pivoted end 1502, and thus defines a semi-circular channel adapted to support at least a forearm of a patient proximate the support structure 100 during e.g. a blood-letting procedure. The pivoting mechanism usefully permits the patient arm support member 1500 to be moved between a stowage position, illustrated in the top perspective view of FIG. 11 and per the left leg member of the bottom end view of FIG. 11, and a use position projecting beyond the vertical plane defined by longitudinally-opposed leg members $120_3$, $120_4$ per the right leg member of the bottom end view of FIG. 11.

Figure 10:
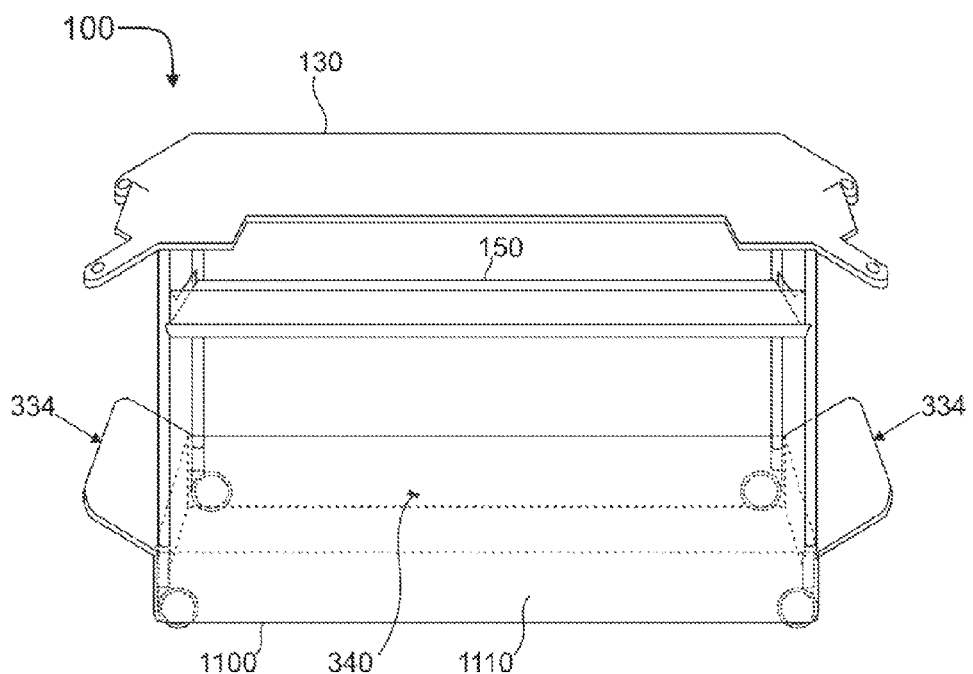
FIG. 10 shows a perspective view of a further embodiment of a medical structure according to the invention, with the base member of FIG. 4B further defining a shroud about the base of the structure.

Still other embodiments may advantageously combine features favouring both mobility in use and modularity, for instance with the adjunction of wheels 600 underneath leg members 120 and, optionally still, wherein the base member 300 shown in FIG. 4A or 4B is replaced with a shrouding base member 1100 shown in FIG. 10, having lateral walls 1110 which form a peripheral shroud about the volume located underneath the top surface 340 of the base member, whilst maintaining sufficient clearance relative to the ground underneath the structure 100 so as not to hinder mobility in use.

Accordingly, it will be readily understood by the skilled reader that the medical support structure 100 of the invention may be manufactured as a plurality of basic components including at least the leg members 120, the top member 130 and the support member 150 and capable of self-assembly by a hospital porter, a nurse or an emergency responder. Such components may be flat-packed for minimal stowage volume and self-assembly may be performed with conventional fasteners and tools such as flathead screws and an Allen key packaged therewith or even, in the case of a disposable embodiment made of recycled material(s), either a suitable glue likewise packaged therewith or a medical glue frequently carried in emergency medical supplies.

The invention is not limited to the embodiments hereinbefore described but may be varied in both construction and detail. For example, it will be readily understood by skilled persons that the inventive principle disclosed herein may be permanently integrated into the base configuration of an item through relevant manufacturing techniques, for instance injection moulding, rather than manufacturing components separately for packaging and subsequent self-assembly.

In the specification the terms "comprise, comprises, comprised and comprising" or any variation thereof and the terms include, includes, included and including" or any variation thereof are considered to be totally interchangeable and they should all be afforded the widest possible interpretation and vice versa.

What is claimed is:

1. A medical support structure comprising
a framework having a main axis and comprising at least one supporting member and a plurality of leg members; and
a top surface locatable atop the framework, adapted to support one or more refuse containers each having an aperture and a bottom portion;
wherein the at least one supporting member is locatable intermediate the top surface and a lower portion of the plurality of leg members, and adapted to support at least one medical waste container having an aperture in an upper portion thereof;
wherein at least a first longitudinal portion of the supporting member forms an obtuse angle relative to a second longitudinal portion of the supporting member so as to angle the or each supported medical waste container-non-orthogonally relative to the top surface in use; and
wherein a portion of the top surface area is recessed above the or each supported medical waste container.

2. A medical support structure according to claim 1, wherein the or each supporting member supports a plurality of medical waste containers to facilitate streaming of medical refuse.

3. A medical support structure according to claim 1, wherein corners at opposed ends of the top surface have a substantially curvilinear shape.

4. A medical support structure according to claim 1, wherein the or each supporting member further comprises a drip tray located substantially underneath the aperture of the or each medical waste container.

5. A medical support structure according to claim 1, wherein a surface of the or each supporting member comprises at least one lodgement for accommodating a lower portion of a medical waste container therein.

6. A medical support structure according to claim 1, wherein at least one end of the top surface comprises a downwardly-angled flange, and a portion of a refuse container wall adjacent the aperture thereof is secured to the downwardly-angled flange with releasable securing means in use.

7. A medical support structure according to according to claim 1, further comprising a base locatable intermediate the or a lowest supporting member and the lower portion of the plurality of leg members.

8. A medical support structure according to claim 1, wherein a height of each leg members is adjustable.

9. A medical support structure according to claim 1, wherein at least one leg member extends through and above the top surface.

10. A medical support structure according to claim 9, wherein a portion end of the at least one leg member extending through and above the top surface, projecting above the top surface, is adapted to support a medical or non-medical device, apparatus or container above and clear of the top surface.

11. A kit of parts for a medical support structure comprising
a framework having a main axis and comprising at least one supporting member and a plurality of leg members; and
a top surface locatable atop the framework, adapted to support one or more refuse containers each having an aperture and a bottom portion;
wherein the at least one supporting member is locatable intermediate the top surface and a lower portion of the plurality of leg members, and is adapted to support at least one medical waste container having an aperture in an upper portion thereof;
wherein at least a first longitudinal portion of the supporting member forms an obtuse angle relative to a second longitudinal portion of the supporting member so as to angle the or each supported medical waste non-orthogonally relative to the top surface in use; and
wherein a portion of the top surface area is recessed above the or each supported medical waste container.

12. A kit of parts according to claim 11, further comprising releasable securing means for securing refuse containers to the top surface.

13. A kit of parts according to claim 11, further comprising a base locatable intermediate the or a lowest supporting member and the lower portion of the plurality of leg members.

14. A kit of parts according to claim 11, further comprising a plurality of wheels, each attachable to a respective one of the plurality of leg members.

15. A kit of parts according to claim 11, packaged for self-assembly by a user.

* * * * *